United States Patent [19]
Kania

[11] Patent Number: 5,830,237
[45] Date of Patent: Nov. 3, 1998

[54] GEL AND CUSHIONING DEVICES

[75] Inventor: Bruce G. Kania, Bozeman, Mont.

[73] Assignee: Ohio Willow Wood Company, Mt. Sterling, Ohio

[21] Appl. No.: 611,306

[22] Filed: Mar. 5, 1996

[51] Int. Cl.$^6$ ........................................... A61F 2/78
[52] U.S. Cl. ........................ 623/37; 623/36; 602/62; 2/22
[58] Field of Search ................... 623/33, 34, 36, 623/901, 37; 425/2; 264/222, DIG. 30; 2/22; 602/62, 63

[56] References Cited

U.S. PATENT DOCUMENTS

| | | |
|---|---|---|
| 1,319,637 | 10/1919 | Blevens . |
| 1,497,219 | 6/1924 | Martino . |
| 2,002,064 | 5/1935 | Kohl . |
| 2,202,598 | 5/1940 | Peterson ..................................... 623/33 |
| 2,666,208 | 1/1954 | Funk . |
| 2,703,405 | 3/1955 | Smallberg, Sr. . |
| 3,451,232 | 6/1969 | Belzidsky . |
| 3,457,566 | 7/1969 | Artzt . |
| 3,520,002 | 7/1970 | Wellington . |
| 3,600,717 | 8/1971 | McKeehan . |
| 3,663,973 | 5/1972 | Spence . |
| 3,855,677 | 12/1974 | Belzidsky . |
| 4,369,284 | 1/1983 | Chen . |
| 4,502,234 | 3/1985 | Schaefer et al. . |
| 4,517,688 | 5/1985 | May et al. . |
| 4,590,123 | 5/1986 | Hashimoto et al. ................. 428/316.6 |
| 4,618,213 | 10/1986 | Chen . |
| 4,635,626 | 1/1987 | Lerman . |
| 4,840,635 | 6/1989 | Smith et al. . |
| 4,908,037 | 3/1990 | Ross . |
| 4,923,474 | 5/1990 | Klasson, et al. . |
| 4,923,475 | 5/1990 | Gosthnian et al. . |
| 5,007,937 | 4/1991 | Fishman et al. . |
| 5,108,456 | 4/1992 | Coonan, III . |
| 5,201,773 | 4/1993 | Carideo, Jr. . |
| 5,201,774 | 4/1993 | Greene . |
| 5,211,667 | 5/1993 | Danforth . |
| 5,218,056 | 6/1993 | Santiyanort et al. ................ 525/332.6 |
| 5,246,464 | 9/1993 | Sabolich . |
| 5,258,036 | 11/1993 | Edenbaum et al. . |
| 5,258,037 | 11/1993 | Caspers . |
| 5,262,468 | 11/1993 | Chen . |
| 5,263,923 | 11/1993 | Fijimoto . |
| 5,263,990 | 11/1993 | Handal . |
| 5,314,496 | 5/1994 | Harris et al. . |
| 5,314,497 | 5/1994 | Fay et al. . |
| 5,376,131 | 12/1994 | Lenze et al. . |
| 5,376,132 | 12/1994 | Caspers . |
| 5,387,245 | 2/1995 | Fay et al. . |
| 5,405,405 | 4/1995 | Love . |
| 5,443,525 | 8/1995 | Laghi . |
| 5,464,384 | 11/1995 | Cromartie ................................. 602/27 |
| 5,464,443 | 11/1995 | Wilson et al. . |
| 5,480,455 | 1/1996 | Norvell . |
| 5,507,834 | 4/1996 | Laghi ........................................ 623/36 |
| 5,555,584 | 9/1996 | Moore et al. ......................... 12/142 N |
| 5,603,122 | 2/1997 | Kania .......................................... 2/239 |

FOREIGN PATENT DOCUMENTS 1 812 982    4/1993    Russian Federation .

OTHER PUBLICATIONS

Brochure—TEC Interface Systems.
Brochure—Silosheath (1994).
Brochure—Alps Clearsheath.
BrochureIpos—Ipocon.
Technical Bulletin—Shell Chemical Company, "Kraton Thermoplastic Rubgers in Oil Gels", Jun. 1992.

*Primary Examiner*—David H. Willse
*Attorney, Agent, or Firm*—Oblon, Spivak, McClelland, Maier & Neustadt, P.C.

[57] ABSTRACT

Articles of apparel for an amputee's residuum and for non-amputees who desire or require padding or joint support.

23 Claims, 9 Drawing Sheets

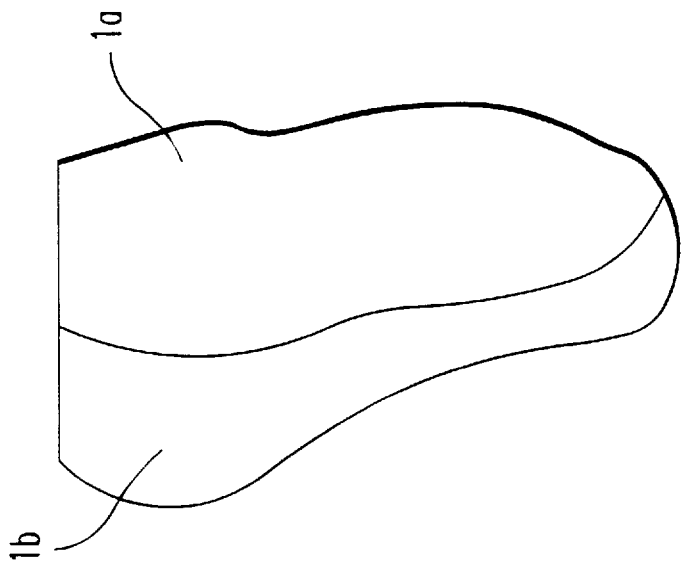
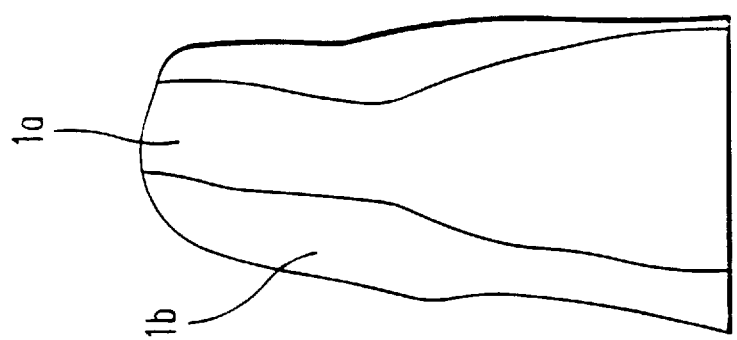

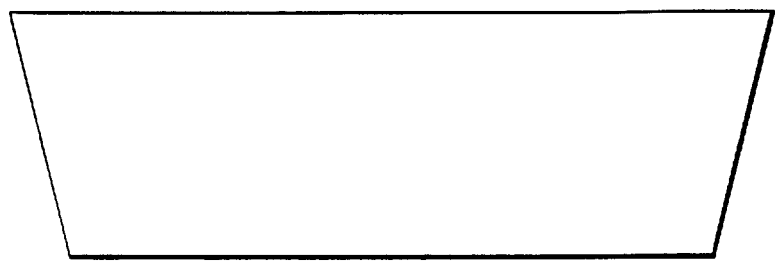
FIG. 3A
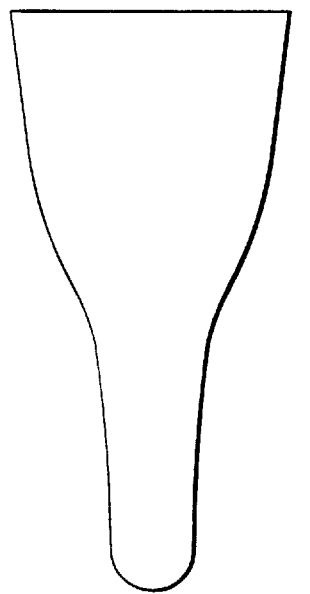 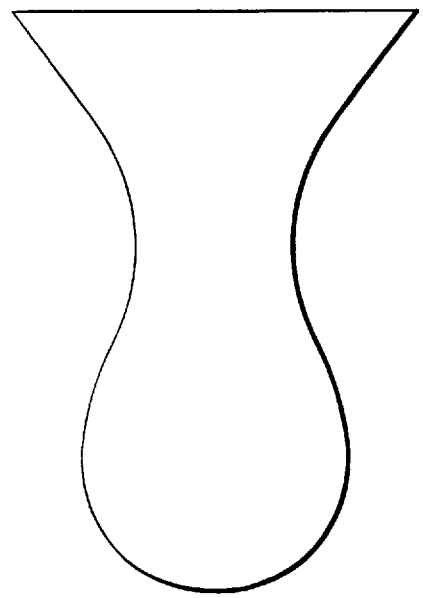
FIG. 3B   FIG. 3C

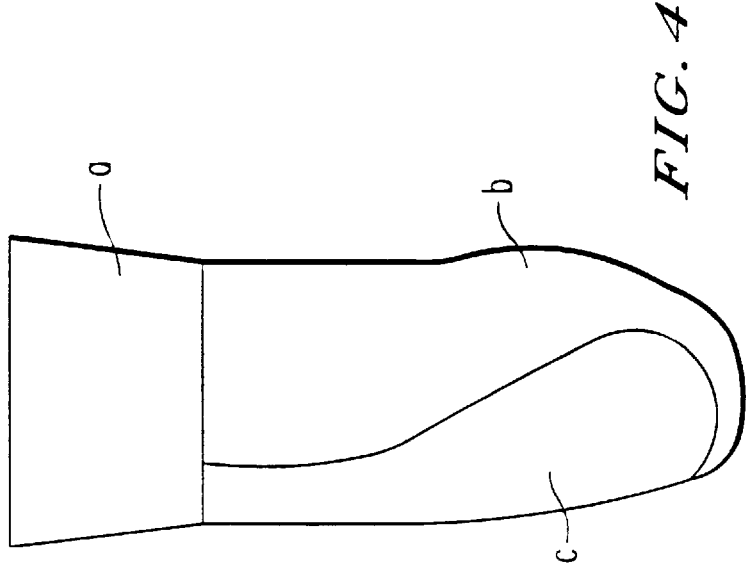

UNIFORM WALL LINER

THINNEST AT THIS END

TAPERED WALL LINER

GEL AND CUSHIONING DEVICES

BACKGROUND OF THE INVENTION

1. Field of the Invention

The present invention relates to a gel and various articles of manufacture such as a cushion liner, cushion locking liner, open-ended cushion knee or elbow sleeve and cushion flat sheet all useful for increasing the comfort of the wearer. Also described is a sleeve member for enclosing an amputation stump, preferably, a cushioned sock for use by, e.g., below-knee (BK) amputees. The sleeve member and cushioning devices are preferably provided in a contoured form fit configuration which adapts to a right or left side bias of the bony prominence of the residuum (stump) or are provided in simple tube (i.e., tube-sock) shape with various optional cushioning. Cushioning material may optionally be provided on the inside and/or outside of the invention sleeves, liners and sheet to minimize the discomfort of, e.g., an orthotic device, such as a knee brace, or a prosthetic device, such as an artificial arm or leg. In a preferred embodiment, the cushioning material is adjusted in thickness and has a non-uniform thickness over the article surface. In another a preferred embodiment the sleeves and liner have cushioning material in a recessed achilles configuration: the cushioning material does not contact the wearer at an upper posterior (i.e., knee crease), or upper anterior (i.e., elbow crease, etc.) portion of the limb or residuum, or minimally contacts the wearer at these positions due, e.g., to the thinning of cushioning material. For example, the cushioning material can be thinner in these areas than in other places.

2. Discussion of the Background

For at least the past 80 years amputees have worn tubular socks over their residual limb. Cotton, wool and cotton-wool blends have typically been used. More recently, with the advent of synthetic materials, nylon and other textiles, including some with a measure of elasticity, have also been utilized.

In a typical below-knee (BK) prosthesis an amputee's stump tends to "piston" in the socket: during ambulation the stump will come up in the socket of the prosthesis until the attaching means holding the prosthesis to the wearer cause the prosthesis to lift with the stump. On the way down, air may be trapped between the residuum and stump sock, or between the prosthesis socket and sock, or between a socket liner and a sock.

With wool and cotton socks which tend to breathe and which are not airtight this pistoning effect is not a major problem with regard to the generation of sound effects. Since wool and cotton tend not to tightly form fit a residuum, however, the amputee typically packs a material around the residuum once it is placed into the prosthetic device or adds additional socks to increase thickness or puts on thicker socks in order to provide necessary fit. However, for socks which do not breathe and which are made from, e.g., polymeric material, a problem occurs when the residuum pistons in the prosthetic device: terrific sound effects such as sucking and gurgling noises are generated which are obtrusive and inappropriate, often embarrassing the wearer. In addition, such air pockets produce non-uniform pressures and loading discontinuities on the skin, irritating it.

Finally, many amputees experience a swelling of the stump. When the residuum is in a prosthetic socket the stump tends to contract significantly, and when taken out of the socket the stump tends to expand within minutes of removal. This expansion and contraction of the residuum contributes to the development of air pockets and the generation of obtrusive noises since a sock which may have provided a comfortable fit on the expanded stump becomes a loose fit with air pocket opportunities when the residuum is placed inside the prosthetic socket. In addition, and over time, an amputee's residuum tends to adjust in size, usually shrinking. As these changes occur they increase the tendency for the pistoning effect, described above, to occur. In addition to the embarrassment caused by the sound effects generated by pistoning, cushioned socks which allow or promote air pocket formation quickly wear out and, if not replaced often, lead to lesions, etc. on the residuum.

Currently available cushioned residuum socks are tubular or conical and do not provide a form fit on an amputee's residuum. Regardless whether such socks are provided with internal and/or external cushioning material they fail to avoid air pockets. While a stump may generally have a roughly conical or cubical shape there are invariably recessed areas on, e.g., the medial side of the prominent tibia bone. Generally, on a below knee, left side residual limb the recessed area will be predominantly on the right side of the tibia bone. There is also typically a smaller recessed area on the left side. For right side residual limbs the predominant recessed area is on the left side of the bone, with smaller recessed areas on the right side. Usually the greatest recess occurs immediately below the patella, on either side. In addition, left side amputees typically have a right side bias to the bony prominence of the below knee stump, and right side amputees have a similar bias to the left side. Conventional tubular or conical elastic socks simply cannot account for these several variable conditions without using extremely high levels of elastic tension which compress the outer-most points along the stump's circumference, causing discomfort and a non-uniform fit.

Amputees typically attach a prosthetic limb to their residual limb by means of a rigid socket, liner, and a suspension means. The rigid socket is often custom fabricated to match the shape of the intended user's residual limb and may be made of thermoplastic or fiber-reinforced thermoset materials, but can also be made from wood, metal, etc. Since such hard materials are generally uncomfortable when in intimate with the skin over long periods of time, especially under load bearing conditions, liners and/or prosthetic socks are often used as interface members between the hard socket and the residual limb to increase comfort. Such liners are generally of the open cell foam type, such as Pelite or Kemblo, but may also be made of silicone, urethane, etc. type materials. See, for example, U.S. Pat. No. 5,258,037 and U.S. Pat. No. 5,376,132, both incorporated herein by reference. Prosthetic socks, as mentioned above, may be made of wool, cotton, synthetic materials, etc, and amputees tend to prefer liners and socks which are easily changed to facilitate cleaning, to accommodate volume changes in the residual limb, or to accommodate different user activities.

Suspension systems which help to hold a prosthetic limb in place may or may not be an integral part of the rigid socket and/or liner. Examples of suspension systems include supracondylar or waist belt, joint and corset systems, neoprene or latex sleeves, socket ears which grip the condyles, suction or pin and lock systems such as those where the pin is attached to a liner and the lock is attached to a hard socket, etc. Examples of typical suspension systems may be found in U.S. Pat. No. 4,923,474, U.S. Pat. No. 4,923,475, U.S. Pat. No. 5,007,937, U.S. Pat. No. 5,108,456, U.S. Pat. No. 5,201,773, U.S. Pat. No. 5,201,774, U.S. Pat. No. 5,246,464, U.S. Pat. No. 5,263,923, U.S. Pat. No. 5,314,497, U.S. Pat. No. 5,387,245, U.S. Pat. No. 5,376,131 and U.S. Pat. No. 5,405,405, all incorporated herein by reference.

However, and as is clear from the above description of the prior art, all current interfaces for use between an amputee's residual limb and a prosthetic device suffer from drawbacks which may include custom fabrication (and corresponding long lead times), high cost, low durability, space requirements (too long, too high profile, etc.), noise due, for example, to air pockets forming between the liner and the residual limb, skin irritation, restricted joint range of motion, lack of accommodation of stump geometry changes, objectionable odors, discoloration, inadequate comfort, etc.

SUMMARY OF THE INVENTION

Accordingly, one object of this invention is to provide a gel which can be used alone or in combination with various other materials such as fabrics and which can be used in or formed into various articles of manufacture, apparel, etc., and used by an amputee and non-amputee to provide increased comfort.

Another object of the present invention is a cushion liner which can fit a range of residual limb sizes with minimal or no air pockets and which comprises, preferably, the invention gel with or without fabric, preferably having a non-uniform thickness throughout.

Another object of the present invention is a cushion locking liner similar to the invention cushion liner but having docking means preferably at the distal end or side thereof for coupling the liner to, e.g., the hard socket of a prosthetic device. The docking means are preferably molded directly into the cushion liner.

Another object of the present invention is an open-ended cushion knee or elbow sleeve which is open on both ends and, when worn by an amputee, can cover the residual limb and prosthetic device so as to provide increased support for the prosthetic device, and when worn by a non-amputee provides padding or joint support.

Another object of the present invention is to provide a cushion flat sheet which is made of gel, of gel and fabric, or of gel and another material which can be used to make any of the invention cushion liners, cushion locking liners, cushion knee sleeves, cushioned socks, etc., and which can be used in other applications where padding is required including shoe inserts, support bracing, seat cushions, sports pads for the knee, shin, elbow, chest, hand, etc., crutch arm pads, etc. The invention cushion flat sheet can also be used as a compression wrap, etc.

Another object of this invention is to provide a novel optionally cushioned sleeve member for enclosing an amputation stump having a form-fitting tubular shape.

Another object of the present invention is to provide an optionally cushioned sleeve member having a bias pattern and contoured form fit which will equally accommodate a left side amputee and a right side amputee.

Another object of the present invention is to provide a cushioned sock, liner, or locking liner having a contoured form fit shape and polymeric cushioning material arranged to provide an interface between an amputee's residuum and a prosthetic device.

Another object of the present invention is to provide a non-cushioned sleeve member having a contoured form fit.

Another object of the present invention is to provide a cushioned sleeve member for enclosing an amputation stump having a contoured, form-fitting tubular shape wherein the interior of the closed end of the sleeve member is impregnated with or coated with a polymeric material arranged in a recessed achilles configuration which provides a cushioning effect at the interface between the residuum and a prosthetic device socket but which minimizes or eliminates contact with the skin in the crease of the knee or elbow.

Another object of the present invention is to provide a cushioned sleeve, open-ended sleeve, sock, liner or locking liner which allows for the timed-release of a skin conditioner, biocide, etc.

Another object of the present invention is to provide a cushioned sleeve for an amputation residuum which is form fitting and which avoids the generation of air pockets and the obtrusive noises they provide.

Another object of the present invention is to provide a sleeve member for enclosing an amputation stump which is form fitting and which is optionally cushioned, which is as thin as possible.

Another object of the present invention is to provide a sock, including typical prior art tube socks, etc., having cushioning material on the inside thereof in a recessed achilles configuration.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 2A and 2B show frontal (A) and side views (B) of the invention sleeve member enclosing a stump-like form, where 1a and 1b refer to pattern members a and b, respectively, in FIG. 1.

FIGS. 3a–3c show a typical pattern for the optionally banded three-piece form fitting sleeve member according to the invention, piece (a) being optional on the FIG. 3 pattern. Piece (a) can also be used in the FIG. 1 pattern to provide a top band.

FIG. 4 shows an invention sleeve member assembled from the FIG. 3 pattern, where a, b and c correspond to patterns a, b and c, respectively, in FIG. 3.

DETAILED DESCRIPTION OF THE PREFERRED EMBODIMENTS

Figure 1A:
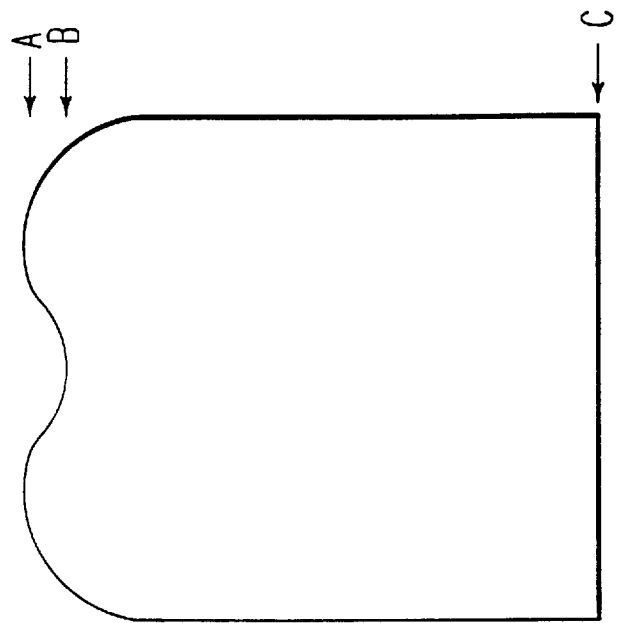
FIGS. 1a and 1b show a typical pattern for the reflected two-piece form fitting sleeve member according to the invention.

The present invention polymeric gel composition comprises, preferably, a block copolymer and mineral oil.

The gels of the invention are nonfoamed or foamed with, e.g., a foaming agent. The mineral oil may be present in from 0–85% by weight based on total weight, more preferably 20–50% by weight, but also including all of any positive amount including 5, 10, 15, 20, 25, 30, 35, 40, 45, 55, 60, 65, 70, 75 and 80% by weight and all values and ranges in between all these listed values. The invention gel preferably has a durometer (Shore A) of 1–20 and preferably a durometer that matches or approximates (±10%) human skin. Preferably, the oil is present on an equal weight basis, or in a weight ratio of 1/4, with regard to the amount of polymeric material present. The polymeric material present is preferably a styrene isoprene/butadiene block copolymer or styreneethylene/butadiene-styrene block copolymer. Preferable examples of such polymeric materials useful herein include C-Flex 1970-W5 (R70-339-000), C-Flex 1960-W5 (both manufactured by Consolidated Polymer Technologies, Largo, Fla., U.S.A.) and Kraton G1654 (manufactured by Shell Chemical Co.). For the C-Flex materials a particularly preferred ratio is 1 part oil per 2 parts C-Flex material.

Preferred ratios of polymer to mineral oil are 1/1–4/1 using C-Flex 1970-W5 or 1960-W5, one part Kraton G1654: 2.75 parts mineral oil, and 14 parts Kraton G1654: 15 parts C-Flex R70-306 (or R70-190 or R70-251 or any mixture thereof): 40 parts mineral oil. The C-Flex R70-339-000, R70-306, -190 and -251 materials are also preferred herein and are products of Consolidated Polymer Technologies. They are blends of S-EB-S block copolymer or SIB block copolymer with mineral oil. 10 parts Kraton G1654 and 11 parts C-Flex R70-306 and 27 parts Duoprime 70 oil is also preferred.

The preferred polymers useful herein and listed above (C-Flex and Kraton materials), in addition to being styreneisoprene/butadiene or styrene-ethylene/butadiene-styrene block copolymers (mixed with mineral oil in the case of the C-Flex R70-339-000, R70-306, -190 and -251 materials) also include styrene-butadiene-styrene and any thermoplastic elastomer having the Shore A characteristics listed above and capable of being blended with mineral oil. Mixtures of all mentioned polymers may be used. Several preferred polymeric materials useful in all aspects of the present invention are more particularly described with regard to the invention sleeve member infra.

The mineral oil used herein is preferably purified mineral oil and is preferably USP grade.

The present invention cushion liner and cushion locking liner may have an overall tube-sock shape or may be form-fitting (described more fully below with regard to the invention sleeve member). These shapes are referred to generically as sock-shaped coverings. The invention sleeve cushion liner and cushion locking liner can fit a range of residual or normal limb sizes with minimal or no air pockets, and preferably have a range of elasticity of from 10–2400% and a range of distal radius of ¾"–4" or whatever is required by the wearer. The invention sleeve, open-ended sleeve, cushion liner and cushion locking liner may be made of the invention gel itself or of a combination of gel/fabric with appropriate seaming, where necessary. At least three standard geometries may be provided for both the invention cushion liner and cushion locking liner, those geometries being 1) uniform wall, 2) tapered wall and 3) contoured wall. These geometries are also useful with regard to the invention sleeve and open-ended sleeve member discussed below and refer to the thickness of the gel. Recessed achilles configuration (see infra) can be used in all articles and aspects of the invention.

Figures 7A, 7B:
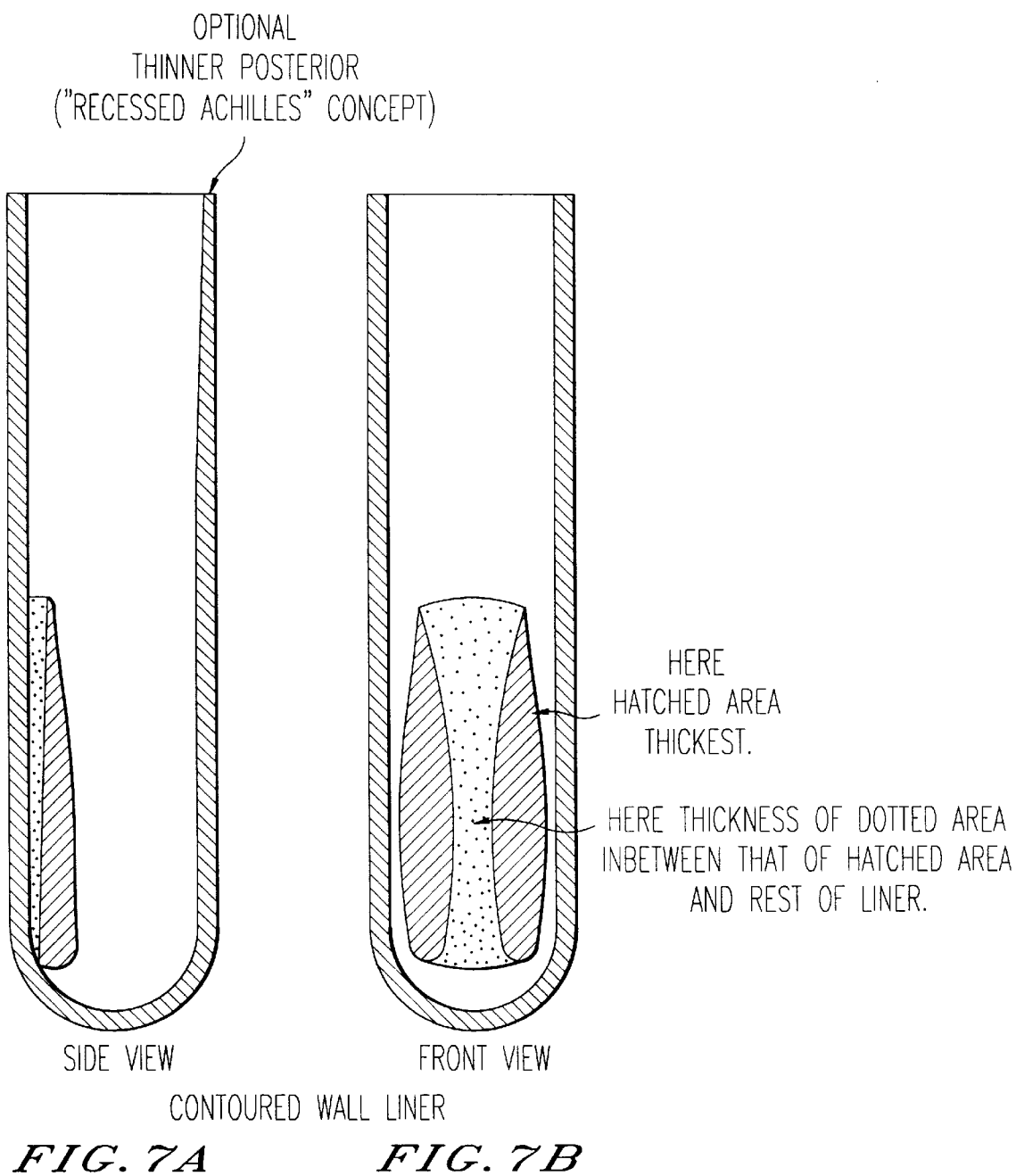
FIGS. 7A and 7B show side and front views of an invention tube sock-shaped cushion liner which has a contoured inner surface providing variable thickness cushioning material at portions of the liner intended to provided particular selective cushioning to the user.
Figure 8:
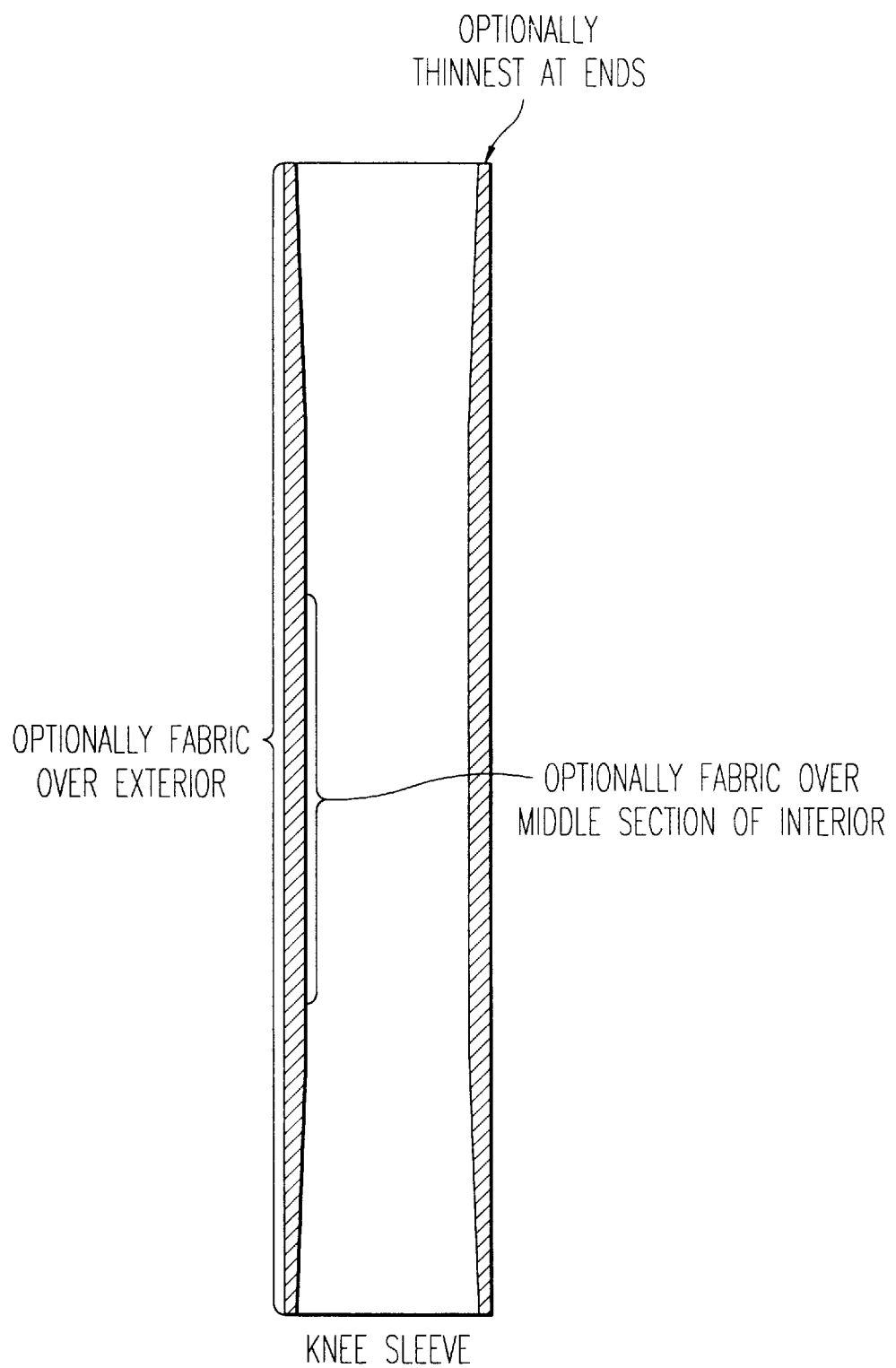
FIG. 8 shows an invention open-ended cushion knee or elbow sleeve with optional fabric covering and with optional thinning at both ends.
Figure 9:
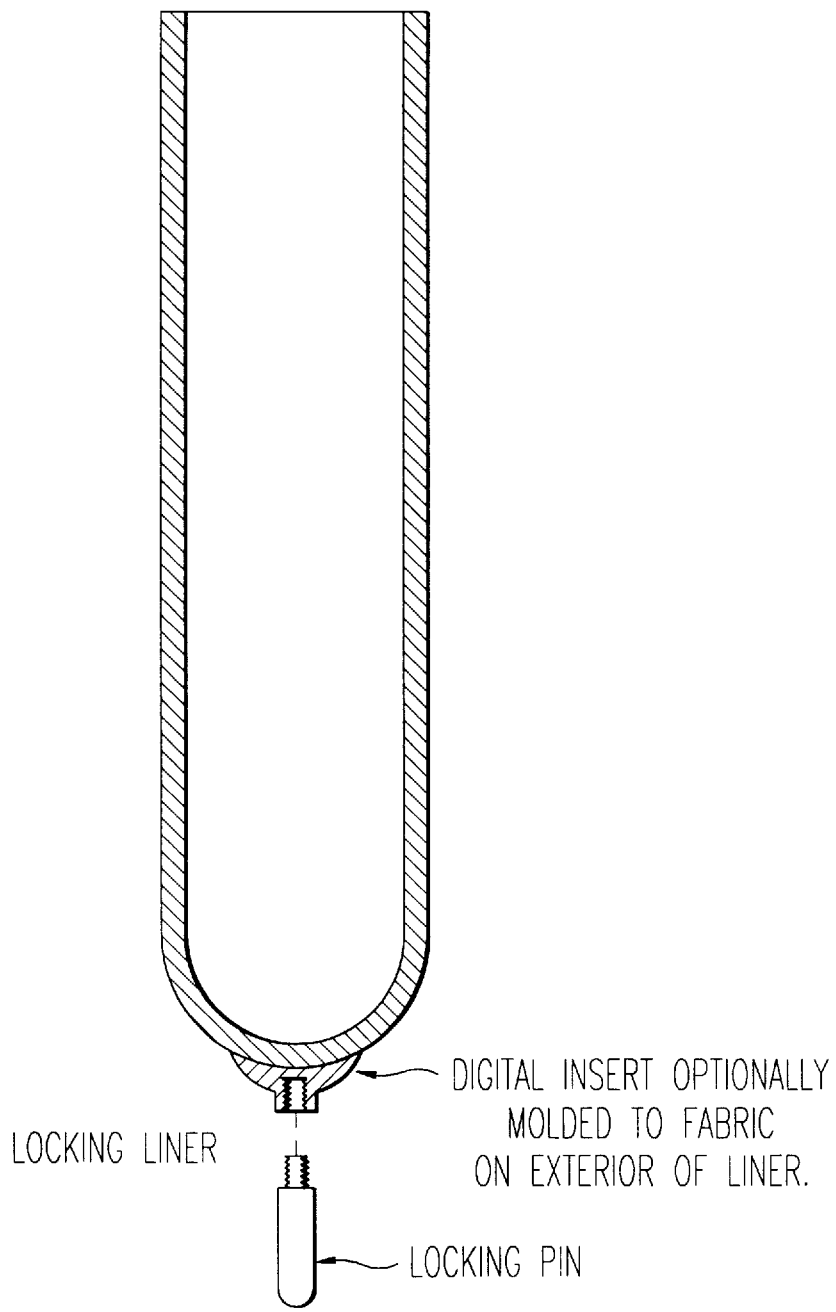
FIG. 9 shows an invention tube sock-shaped locking liner with docking means at the distal end thereof.
Figure 10:
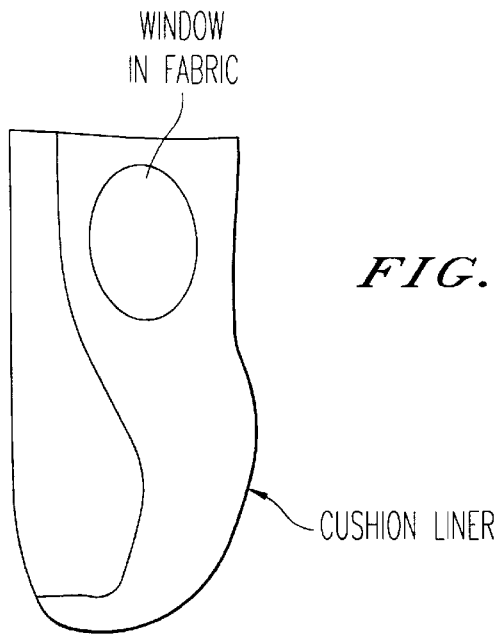
FIG. 10 shows an invention form fitting sleeve having an optional window of clear plastic material, etc., in the fabric.
Figure 11:
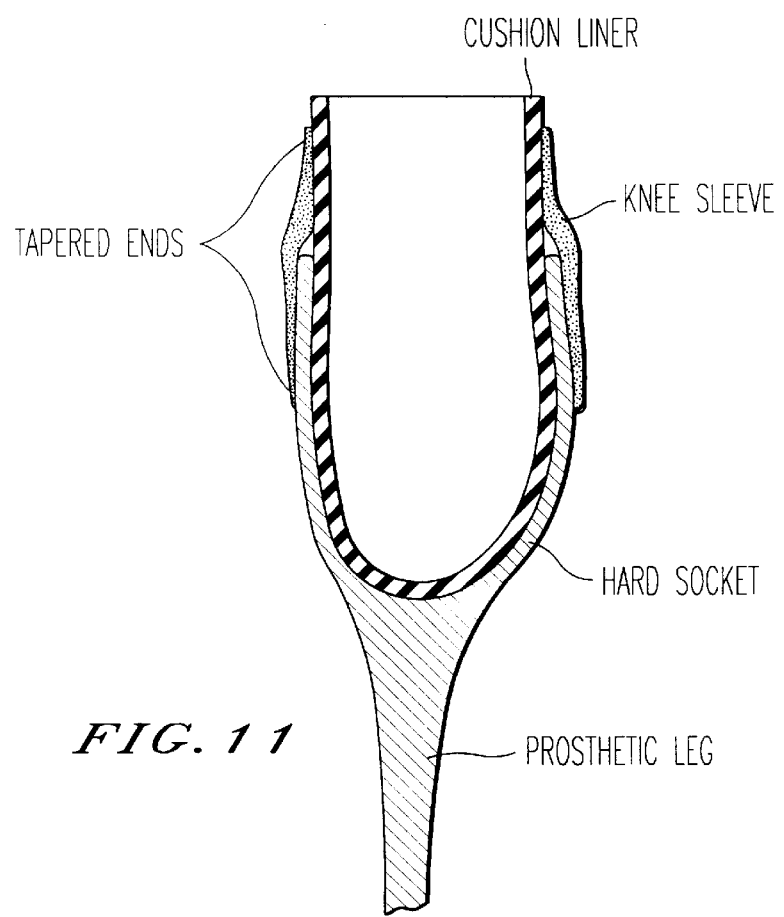
FIG. 11 shows an invention open-ended knee or elbow sleeve in position and contacting a cushion liner and a prosthetic device.

The uniform wall cushion and cushion locking liner simply comprise a uniform thickness of gel. Tapered wall cushion liners and cushion locking liners are generally those having a layer of gel which is thicker distally for additional padding (and because most shrinkage of the residual limb occurs at this point of the limb) and thinner proximally (near the open end of the liner) to blend in and interface more easily with the residual limb. Contoured wall cushion liners and cushion locking liners have uneven distribution of gel throughout to provide cushioning effects where needed and, in a preferable embodiment, have a thinner posterior middle and upper to allow maximum range of motion optionally with a thicker distal end both anterior—medial and anterior—lateral with less thickness in the region between these two areas so as to pad typical bony promenances. Contoured wall liners are often thicker distally and custom shapes can easily be provided to satisfy the individual user. For example, in the liner of FIG. 7, the hatched area has a gel or polymeric material cushion thickness of 13 mm, the dotted portion 11 mm, the front of the liner 9 mm and the portion for behind the knee less than 9 mm.

For both the invention cushion liner and cushion locking liner combinations of gel with fabric include gel with a two-piece or three-piece form-fit sleeve (described below). Other configurations include gel coating inside a tube-sock fabric form.

Foamed or nonfoamed thermoplastic elastomers or rubber only can also be used as cushioning material alone or in combination with the invention gel in all the articles of the invention. The term "thermoplastic elastomers" has its typical meaning and excludes the invention gel. The foamed materials can exclude mineral oil. The inclusion of thermoplastic elastomers in the invention gel (the mixture optionally being foamed) is advantageous in making the products customizable since such products will tend to take the shape of a limb or model of a limb when, e.g., heat and/or pressure are applied. In a preferred embodiment the invention gel can be foamed and used alone or in combination with fabric in all forms of the invention including the sleeve member (open-ended or closed), in the form of a tube-sock, etc.

In addition, in the present invention articles of manufacture including the cushion liner, cushion locking liner, cushion knee sleeve, cushion flat sheet and sleeve member, transducers can be included therein to sense pressure, force, temperature, etc., to detect and/or transmit a signal from the residual limb to a prosthetic device, to send myoelectric signals, etc. In addition to transducers, any electrical device or other sensing device can be similarly incorporated for detection, signal transduction, etc. See, for example, U.S. Pat. No. 5,443,525, incorporated herein by reference.

As mentioned above, the invention cushion locking liner comprises docking means for attaching an external device, etc. to the liner. Such docking means includes pins, etc. and are typically those which help to attach and support a prosthetic device. These docking means are known in the art and are preferably incorporated in the cushion locking liner by means of direct molding, meaning the injection molding of an adapter into the fabric, etc. Such docking means, including distal inserts, can be centered or can be offset to accommodate individual residual limb geometries. Other docking means include molding a raised configuration in the side of the liner which then mates with a recess on the inside of the prosthetic socket, allowing for a locking effect when the user dons the liner and steps into a socket.

The invention open-ended cushion knee or elbow sleeve (also referred to herein as cushion knee sleeve or knee sleeve, etc., for brevity) is intended to be worn by an amputee and provide an interface between the residual limb and a prosthetic device, and is worn external to both or may be worn by a person whose limb is intact but desires or requires padding or joint support. The knee sleeve is generally cylinder- or band-shaped and covered on the exterior with fabric and coated on the inside with invention gel. The sleeve can be any size but typically is from 1–25 inches long including 10, 15, 16, and 20 inches, and any diameter (unstretched) such as 1–10 inches, including 2, 3½, 4 and 5 inches. Fabric may cover the middle section of the interior, if desired. The cushion knee sleeve itself may have a conical (i.e., tapered) shape with a smaller diameter distally than proximally or smaller diameter distally and proximally as compared to a central diameter so as to grip and hold the prosthetic device or residuum at the smaller diameter end(s). The interior gel coating can be thinner at either or both of the distal and proximal end, and can be thinner or absent in the back of or whole of the middle section thereof so as to not bind in the crease of the knee or elbow when worn by the user. It is preferred that the wall thickness of the gel be thin at the ends regardless whether there is fabric covering the gel or whether the exterior or whole cushion knee sleeve is made simply of gel itself.

The invention cushion knee sleeve can be used in combination with the invention sleeve, cushion liner or cushion locking liner as a means for suspension of a prosthetic device, or can be used alone. In addition, the invention knee sleeve can have attached thereto, by molding into the gel, by attachment means such as pins, etc., an orthotic knee joint and optional support bars such that the sleeve constitutes a knee brace.

All the invention articles such as the (closed-ended) sleeve and liners can be provided with gel or thermoplastic on the outside thereof so as to come in contact and provide increased friction with the interior gel of the cushion knee sleeve. Such a configuration provides additional support and suspension of the prosthetic device.

The present invention sleeve member for enclosing an amputation stump overcomes the problems encountered with prior art tubular or conical socks which are either prone to air pocket sound effects or are so constricted as to be uncomfortable by providing a sleeve member which is made in the shape of or from a pattern and comprises the invention gel, a textile material, combination thereof, elastomer, or textile material with other elastomer which provides elastic tension such that the sleeve member form fits an amputee's residuum. This combination of sleeve pattern in the form of gel, or gel and textile material or textile material alone, etc. provides a sleeve member having a comfortable feel and avoiding the generation of obtrusive sounds which are directly traceable to the presence of air pockets between a sleeve member and an amputee's residuum or between sleeve member and prosthetic socket.

In all aspects of the invention described herein, the elasticity of the fabric and/or gel and/or elastomeric material is preferably sufficient to accommodate the swelling or shrinkage of the residual limb typically experienced by an amputee and still maintain an intimate fit. The sleeve of the invention has enough elastic compression to form fit a stump but is not so tight as to be considered a stump shrinker, as in U.S. Pat. No. 4,840,635 incorporated herein by reference.

Figure 1B:
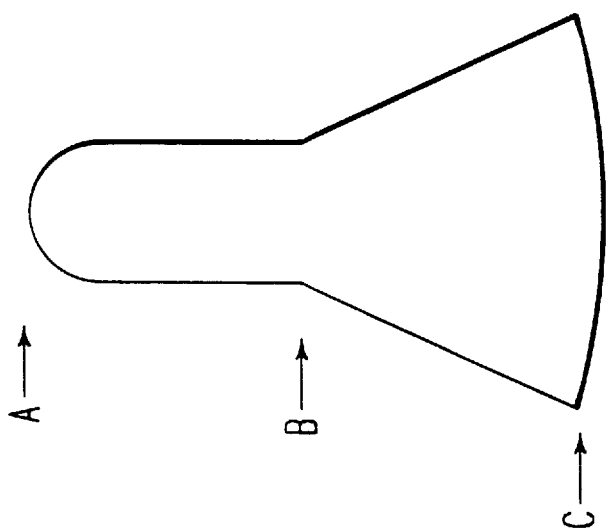
Figure 5:
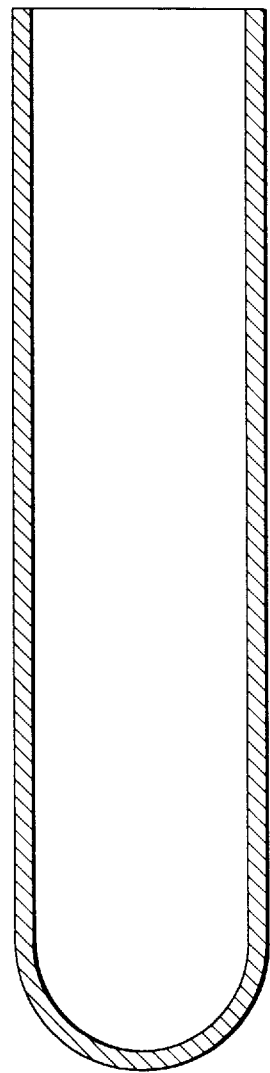
FIG. 5 shows a tube sock-shaped cushion liner according to the present invention with uniform wall thickness.
Figure 6:
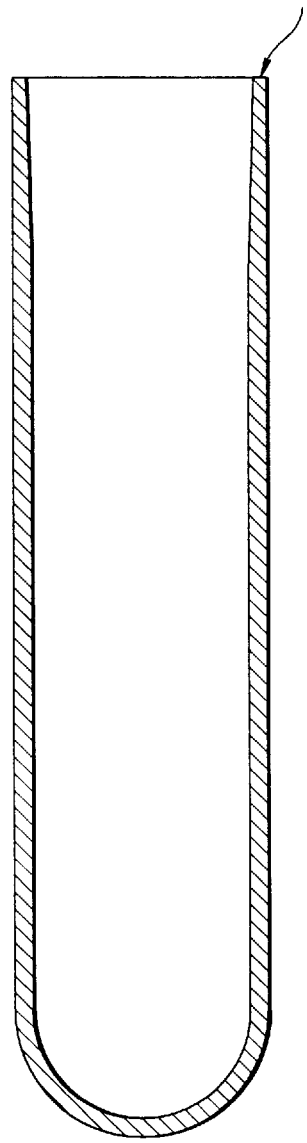
FIG. 6 shows a tube sock-shaped cushion liner according to the invention having a tapered wall thickness at the open end.

FIG. 1 depicts a typical pattern from which the present invention form-fitting sleeve member is constructed or shaped into. The pattern is a reflected two-piece pattern, one piece of which is designed to cover the bony prominence of a typical BK stump, (FIG. 1a) the other piece joined to the first at the edges thereof and circumscribing the typical onset of soft tissue around the stump (FIG. 1b). The two patterns can be used to cut out two or more pieces of textile material which are brought together such that the "X" on each of the patterns in FIGS. 1a and 1b are in contact with the "X" on the other pattern, followed by the sewing together of the edges of each pattern in typical fashion. When the two pieces are sewed together, a sleeve member is provided which has a form fitting residuum-like (tubular) shape having an open end into which an amputation stump may be introduced, a closed end opposite to the open end, an interior and an exterior. The two-piece pattern may be cut out of the same textile material or different textile materials, and the two pieces of textile material may have the same color or different colors. The three-piece optionally banded reflected pattern of FIG. 3 also provides a form-fit sleeve, piece (a) being optional. In the case of a product made of invention gel alone, thermoplastic alone or combination thereof, the gel is shaped into the patterns depicted in FIGS. 1 and 3 by art-accepted means using molds, etc.

The form fit sleeve of the invention can be made from fabric, gel, elastomer, and combinations thereof according to the patterns in FIG. 1 or FIG. 3. In FIG. 1a the distance A–B divided by the distance B–C generally varies from 2/1 to 1/2 and is preferably about 1/1. The width of the pattern in FIG. 1a at point B divided by the width at point C is generally approximately from 1/4–1/1, preferably about 1/2. In FIG. 1b the distance A–C divided by the distance B–C is generally preferably about 1.05–1.3, most preferably about 1.1. In both patterns of FIGS. 1 and 3 the dimensions may be varied so as to provide a comfortable form fit that avoids air pockets.

The two or more pieces of textile material used to form the invention form fitting sleeve member can be sewn together using any type of thread and any type stitch. This is also true for tube-sock shaped articles. In a preferred embodiment, woolly nylon is used to interconnect the two-piece or three-piece form-fitting sleeve member of the invention or seam the tube-sock using a flat-locked stitch, which is a stitch well known to those in the art. This flat-locked stitch tends to create a smooth, non-irritating seam having a stretch comparable to jersey fabric.

The size of the sleeve member according to the invention can be varied depending upon the residuum to be enclosed by simply proportionally reducing or enlarging the pattern, as desired. The term "form fitting" residuum-like (tubular) shape as used herein refers to the shape of the invention sleeve member which provides a contoured fit on an amputation stump, which substantially reduces or eliminates air pockets during pistoning of the amputation stump in a prosthetic socket and which is obtained by providing a sleeve member composed of two or more pieces of fabric having the pattern described in FIG. 1 or FIG. 3 and/or comprised of invention gel and/or other elastomeric material in the shape provided by these patterns. Residuum-like configuration is further achieved via a bias molding technique that replicates contours of a normal amputation stump.

The fabric-containing articles according to the present invention may be made with any textile material having any thickness (ply). Preferred textile fabrics are those having elasticity, including elasticities of 10–400%, such as stretchable non-wovens (e.g., the Xymide line of fabrics including Wearforce® fabrics from DuPont which connect bulkable yarns with non-woven sheet substrates), Lycra® comprising segmented elastomeric polyurethane fibers (spandex), supplex nylon (an engineered nylon textile fabric with a cotton-like texture and appearance), neoprene fabrics (polychloroprene fabrics), nylon, spunbonded olefin, looped nylon, spunlaced fabrics, polyester, aramid fiber fabrics, etc. However, any textile material may be used such as those described in *Textiles,* fourth edition, N. Hollen et al, MacMillan, New York, 1973, *The Modern Textile Dictionary*, Duell, Sloan and Pearce, New York, 1963 and *Dyeing Chemical Technology of Textile Fibers,* Trotman, E., Charles Griffin and Co., London, 1975, all incorporated herein by reference. The fabrics used to make the invention articles are preferably elastic and are preferably jersey knit but include all woven, knitted and non-woven textile fabrics. In addition to those mentioned above and described in the above-mentioned references, those described in Volume 22, p. 762 ff and Vol. 16, p. 72 ff of the Kirk-Othmer *Encyclopedia of Chemical Technology,* Wiley, New York, 1983 and 1981, respectively, are also included, both of these references being incorporated herein by reference. Mixtures of types can be used with seaming where necessary.

Preferred fabrics include mixtures of the above-mentioned fabrics, such as a fabric of neoprene, 88% supplex nylon/12% lycra spandex, 85% nylon/15% lycra spandex, 94% polyester/6% lycra spandex. Such mixed fabrics may be uniformly mixed or may have one type of fiber or predominantly one type of fiber on one face thereof. For example, in those fabrics described above which contain lycra, the lycra can be mixed throughout, can make up the entire or substantially the entire face, or the entire or substantially the entire back of the fabric once it is arranged in an invention article.

The textile fabrics used in the invention may be treated/finished in any manner known in the art. For example, a nylon tricot surface may be applied to the textile fabric, etc. The finishing need not be uniform over the entire invention article. The article may be selectively treated at, for example, above the knee (or elbow) portions, and with the same treatment, no treatment or another treatment being present below the knee or elbow. Similarly, treatment on the outer surface of the invention sleeve member may be different from that on the inside thereof.

The textile material used to make the invention articles is preferably elastic (stretchable) in one or more, preferably two, directions and is capable of adjusting to variations in form and size of the residuum or limb. In a preferred embodiment, a nylon, neoprene, looped nylon combination provides excellent comfort and durability. Preferred thicknesses of the invention textile material range from 0.010 in–0.200 in, preferably 0.025 in to 0.125 in, all values and all ranges therebetween. Typically the thicknesses of patterns pieces in FIGS. 1 and 3 are the same, but need not be.

The sleeve member according to the invention is preferably a cushioned sleeve member, that is a sleeve member having a form fitting shape with an open end into which an amputation stump may be introduced, a closed end opposite to said open end, an interior and an exterior, wherein the interior at the closed end is impregnated with a polymeric material arranged so as to provide a cushion between the amputee's residuum and any prosthetic device to be worn, attached to, etc. the residuum. The cushioning material is preferably a polymeric material, most preferably the invention gel and/or a thermoplastic elastomer (referred to simply as thermoplastic herein) such as a thermoplastic rubber, silicon containing elastomer, etc. which provides an interface between the residuum and a prosthetic device but which does not contact or minimally contacts the skin at the back of the knee or elbow when worn by an amputee (recessed achillies). This cushioning material may also here and in other articles of the invention be a thermoset silicone. This cushioning material is thus provided in a "recessed achilles" arrangement which avoids the irritation occurring in the crease behind a knee or elbow provided by prior art cushion sleeves by thinning or eliminating cushioning polymeric material at this location. If the form fit sleeve is to be worn by an above-knee amputee the recessed (thinned or absent) portion of the cushion material may be arranged medially at, e.g., the perineum for increased comfort.

The polymeric material which provides the cushioning effect in all aspects of this invention may be any polymeric material. Preferred materials other than the invention gel and those described above are those elastomers described at pgs. 446–640 of Volume 8 of the Kirk-Othmer *Encyclopedia of Chemical Technology*, Wiley, New York, 1979 and those rubbers described in *Synthetic Rubbers: Their Chemistry and Technology,* Blackley, D., Applied Science Publishers, London, 1983 and *Rubber Technology*, Morton, M. Ed., Van Nostrand Reinhold Co., New York, 1987, all three references incorporated herein by reference. A preferred embodiment of the present invention sleeve member, when cushioned, includes a cushioning material of Kraton®-type rubber material including those obtained from Shell, CPT, and GLS. These Kraton® rubbers are styrene-ethylene/butylene-styrene block copolymers or styrene-ethylene/propylene block copolymers or styrene isoprene/butadiene block copolymers and are available in triblock or diblock form. See, e.g. the *Kraton® Technical Bulletin* from Shell Chemical Company, SC:1102–89, June, 1992, incorporated herein by reference.

The cushioning polymeric material used in the present invention cushioned sleeve member is characterized by a certain durometer range. Durometers for the invention cushioning material preferably range from 1–20 on the Shore "A" scale. The lower the number the softer the material, typically due to a higher level of plasticizer. One preferred durometer range is 3–14 including all values therebetween and all ranges therebetween.

The invention polymeric cushioning material may be a blend of, e.g., Kraton® rubbers and oils such as mineral oil, etc. including typical stabilizers, etc. which provide an average durometer of from 1–20, preferably 3–14. These blends typically comprise a rubber having a lower durometer (1–10 on the Shore "A" scale) and a rubber having a higher durometer (e.g., 11–20). The blends are preferably capable of being stretched 100% or more, preferably 400% or more before tearing and are capable of providing a form fit to the residuum due to their inherent elasticity. In addition, low durometer Kraton® rubbers and other materials tend to have a sticky feeling which, when present in the polymeric cushioning material, tends to enhance the form fitability of the sleeve essentially by mating against the skin.

In donning those articles of the invention which, when worn, provide contact between, e.g., the invention gel, a thermoplastic material, a combination thereof, etc., with the skin and/or a prosthetic device it is preferred that the invention article be donned in a manner such that the polymeric material does not drag against the skin. For example, the invention cushion liner or sleeve can be rolled before donning, and then unrolled on the limb and/or device. In this manner, the cushioning polymeric material encloses the limb and/or device without sliding or friction. If the invention article has an outer textile surface, the textile material slides against itself, providing easy action. With regard to the open-ended sleeve described herein a particular advantage is obtained when this open-ended sleeve has an interior middle band of fabric. The distal and proximal portions of the open-ended sleeve can be rolled towards the middle of the sleeve, and the sleeve can be donned with contact between the wearer or device and fabric only. The thermoplastic-containing portions can then be unrolled onto the wearer and/or device. In all cases, the invention articles can be taken off by reversing the above-describe processes. This aspect of the invention (easy donning and doffing) is an important advance in the art provided by the present invention. No lubricant, talcum powder, etc. is required, as with currently available materials. In addition, the invention articles, regardless of their composition, can be adapted such that the portion thereof which will come in contact with the user's apparel such as pant legs, shirt sleeves, etc. is fabric or covered with fabric such that the wearer's apparel does not stick to and bunch on the invention articles.

If desired, the present invention cushioning material may comprise antioxidants such as Vitamins A, B and C or any other antioxidants commonly used in polymers which can weep out on a time release basis. In addition, skin conditioning agents may be added to the polymeric material of the present invention to soothe the skin during wear. Such skin conditioners include mineral oil, baby oil, etc. which may be added to the polymeric material prior to its application to the sleeve member. Also, astringents, biocides, medicaments, etc. may be added or applied to the cushioning material to avoid infection or heal sores, etc.

As described above, the cushioning material of the present invention is preferably formed in a recessed achilles fashion on the interior of the invention articles. Cushioning material may also be applied to the exterior. In both cases, it is preferred that the cushioning material be applied such that it provides an interface between the amputee's stump and a prosthetic device or provides padding and/or joint support but minimizes or eliminates contact with the skin at the back of the knee or elbow when worn. The cushioning material may be separated from the skin by a piece of fabric, by an interior sock liner, or may contact the skin directly. Such contact with the skin can reduce sweating, etc.

While several methods may be used to apply the cushioning material to fabric, a preferred method includes the dipping of the closed end of the invention article into molten or liquified cushioning material at an angle of from 15° to 80°, preferably 20°–50°, most preferably 24°–45°, with respect to the surface of the molten or liquid cushioning material. In this manner, the cushioning material extends up the article from the closed end thereof to a further extent on the side of the liner, sleeve, etc. to be positioned in front of the knee than behind the knee (e.g., the pattern in FIG. 1a faces forward on a BK amputee). As long as the cushioning polymeric material minimizes or eliminates contact with the skin at the back of the knee or elbow when worn but still provides an interface between the amputee's stump and a prosthetic device or provides join support and/or padding, the material is in a recessed achilles configuration. Preferably the polymeric material comes up at least about ½–18, preferably ½–10, more preferably 3–8 inches, including all values and ranges therebetween these several values, from the closed end of the articles in front of the knee or elbow and covers the knee. The difference in height of the cushioning material behind (i.e., in the crease of) the knee or elbow as opposed to in front of the knee or elbow can differ by several inches measured from the closed end of the article, typically from 1–15 inches, preferably 1–8 includes and all values therebetween and all ranges therebetween these several values. In a preferred embodiment the cushioning material is thicker at the closed end of the article than it is towards the open end.

In addition to the application of the invention gel and/or polymeric cushioning material to, e.g., the sleeve member by dipping into liquified or molten polymeric material or painting the material on the article, etc., it is possible to dissolve the polymeric material in a solvent followed by application of the solvent to the article with subsequent evaporation of the solvent. Close control of the thickness of the polymeric material is obtained using this method. In both the direct dipping and solvent methods the article is generally spun with distal end angling downward to provide tapered thickness while drying. In general, the thickness of the polymeric material applied to the invention articles in any fashion including in a recessed achilles fashion can be any thickness to, e.g., several inches, but preferably varies from 0.001–0.500 inches, preferably 0.011–0.150 inches but all values and all ranges therebetween these several values, and can be substantially nonconstant in thickness throughout. For example, the cushioning material preferably may be thicker at the closed end of the sleeve (e.g., 0.125 in thick) and be tapered or feathered in decreasing thickness as the open end is approached. Such changes in thickness can be accomplished by techniques known to those of ordinary skill in this art and are within their skill. For example, compression molding can be used.

Another preferred method of producing the invention articles is injection molding. The article is pulled over a core and inserted into a cavity with polymeric material being injected into the cavity.

Other features of the invention will become apparent in the course of the following descriptions of exemplary embodiments which are given for illustration of the invention only and are not intended to be limiting thereof.

EXAMPLES

Example 1

A form-fit next-to-skin sock was prepared from an 88% supplex nylon/12% lycra spandex jersey knit fabric using woolly nylon thread and a surged flat-locked stitch. The sock comprises two pieces of fabric, the first piece having the pattern described in FIG. 1a, the second piece having the pattern described in FIG. 1b.

A mixture of melted Kraton® rubbers obtained from Shell (G1652) and GLS (6705) and Duoprime® 70 oil (mineral oil) was prepared, the sewn inverted sock was then placed over a mold facsimile of an amputation stump having recessed portions at what would be either side of the tibia and dipped into the molten Kraton® blend at an angle of 24°–28° with regard to the plane of the surface of the molten Kraton® and removed. The mold was spun during drying. A form-fit cushioned stump sock was obtained having adhered cushioning material in a recessed achilles arrangement on the interior thereof.

Example 2

A ¹⁄₁₆ inch thick neoprene textile fabric with nylon tricot surface treatment for above the knee contact was used to prepare a three-piece form fitting sleeve member according to the present invention using the pattern described in FIG. 3. The ¹⁄₁₆ inch neoprene material for the below the knee segment of the invention sleeve had nylon on the exterior side and looped nylon on the interior side. The against the skin side of the above knee segment of the invention sleeve was neoprene which provided a high friction bond. This form fitting sock was dipped into molten Kraton® (a blend of tough and soft Kraton® used in Example 1) at an angle of 24°–28° to provide a cushion material on the interior thereof. The resultant composite sock of nylon, neoprene, looped nylon and cushioning rubber provides a durable cushioned sleeve member which, when impregnated with rubber, has an approximate thickness of ⅛ inch.

Example 3

A polartec 2000 stretch laminate fabric having an 85% nylon/15% Lycra® spandex face and a 94% polyester/6%

Lycra® spandex back was used to prepare an invention sleeve member using the pattern described in FIG. 1. The resultant sleeve member is a form-fitting tubular member for enclosing an amputation stump.

Example 4

A commercial cotton tube sock is inverted and dipped into molten elastomer at an angle of 26° relative to the plane of the molten elastomer. A sock having cushioning material in a recessed achilles configuration is obtained.

Example 5

A 2-piece form fitting sleeve was made from a fabric containing 57% polyester, 33% nylon, and 10% lycra and was placed over a core pattern. A mixture of molten C-Flex 1970-W5 (67 wt %) and Duoprime 70 mineral oil (33 wt %) was poured into a cavity and the core with sleeve was placed in the cavity to produce a cushion liner.

Example 6

A 2-piece form fitting sleeve was made of a nylon/Lycra materia. An adapter was injection molded into the closed end of the sleeve with polypropylene. The sleeve with adapter was then inverted and placed over a core. A mixture of molten C-Flex 1970-W5 (50 wt %) and Duoprime 70 mineral oil (50 wt %) was poured into a cavity and the core with sleeve was placed in the cavity to produce a cushion locking liner. After molding, a pin was threaded into the adapter which was adapted to mate with a lock built into a prosthetic socket.

Example 7

One end of a tubular knitted terry stockinette was sewn closed and the open end was slid over a core pattern. A mixture of molten C-Flex 1970-W5 (57 wt %) and Duoprime 70 mineral oil (43 wt %) was poured into a cavity and the core with stockinette was placed in the cavity. Once the gel had cooled, the stockinette with gel was removed and the closed end cut off to produce a cushion knee sleeve.

This application includes the subject matter of U.S. application Ser. No. 08/406,145 incorporated herein by reference. The material safety data sheets and product brochures of the commercially-available materials mentioned herein are also incorporated herein by reference.

The invention articles are designed primarily for the human wearer, and thus are sized appropriately. Diameters typically vary from 1–8 inches (unstretched) and overall lengths typically vary from 1–30 inches (unstretched). Obviously, numerous modifications are available which fall within the scope of the invention and appended claims.

What is claimed as new and desired to be secured by Letters Patent of the United States is:

1. A tube sock-shaped covering for enclosing an amputation stump, said covering having an open end for introduction of said stump and a closed end opposite said open end, said covering comprising fabric in the shape of a tube sock coated on only one side thereof with a foamed or non-foamed gel composition comprising a block copolymer and mineral oil.

2. The tube sock-shaped covering as claimed in claim 1, wherein said gel has a thickness profile such that the gel is thicker at the closed end of the covering than at the open end.

3. The tube sock-shaped covering of claim 1, wherein said gel coating is on the inside of said covering and is arranged in a recessed achilles configuration.

4. The tube sock-shaped covering as claimed in claim 1, wherein said gel has a uniform thickness profile.

5. The tube sock-shaped covering as claimed in claim 1, wherein said gel is provided in an uneven thickness distribution throughout.

6. The tube sock-shaped covering as claimed in claim 1, wherein said block copolymer is a styrene isoprene/butadiene block copolymer.

7. The tube sock-shaped covering according to claim 6, wherein said gel composition is a non-foamed gel composition.

8. The tube sock-shaped covering according to claim 7, wherein said gel composition comprises 60–85% by weight mineral oil.

9. The tube sock-shaped covering according to claim 8, wherein said gel is arranged in a recessed achilles configuration, and wherein said gel has a thickness of 0.150–0.500 inches in areas of said covering not adapted to contact the back of the knee or elbow when worn by an amputee.

10. The tube sock-shaped covering as claimed in claim 9, wherein said fabric is a stretchable fabric having an elasticity of 10–400%.

11. The tube sock-shaped covering as claimed in claim 9, wherein said gel composition has a Shore A Durometer of from 1–20.

12. The tube sock-shaped covering according to claim 6, wherein said gel composition has a thickness of 0.150–0.500 inches.

13. The tube sock-shaped covering as claimed in claim 1, wherein said block copolymer is a styrene-ethylene/propylene block copolymer.

14. The tube sock-shaped covering as claimed in claim 1, wherein said block copolymer is a styrene-ethylene/butadiene-styrene block copolymer.

15. The tube sock-shaped covering according to claim 1, wherein said gel composition is a non-foamed gel composition.

16. The tube sock-shaped covering as claimed in claim 15, wherein said gel composition has a thickness of 0.150–0.500 inches.

17. The tube sock-shaped covering according to claim 15, wherein said gel is arranged in a recessed achilles configuration, and wherein said gel has a thickness of 0.150–0.500 inches in areas of said covering not adapted to contact the back of the knee or elbow when worn by an amputee.

18. The tube sock-shaped covering according to claim 1, wherein said gel composition comprises 60–85% by weight mineral oil.

19. The tube sock-shaped covering as claimed in claim 18, wherein said fabric is a stretchable fabric having an elasticity of 10–400%.

20. The tube sock-shaped covering as claimed in claim 1, wherein said gel composition has a thickness of 0.150–0.500 inches.

21. The tube sock-shaped covering as claimed in claim 20, wherein said fabric is a stretchable fabric having an elasticity of 10–400%.

22. The tube sock-shaped covering as claimed in claim 1, wherein said fabric is a stretchable fabric having an elasticity of 10–400%.

23. The tube sock-shaped covering as claimed in claim 1, wherein said gel composition has a Shore A Durometer of from 1–20.

* * * * *

(12) EX PARTE REEXAMINATION CERTIFICATE (6412th)
United States Patent
Kania

(10) Number: US 5,830,237 C1
(45) Certificate Issued: Sep. 2, 2008

(54) GEL AND CUSHIONING DEVICES

(75) Inventor: Bruce G. Kania, Bozeman, MT (US)

(73) Assignee: The Ohio Willow Wood Company, Mt. Sterling, OH (US)

Reexamination Request:
No. 90/008,277, Oct. 5, 2006

Reexamination Certificate for:
Patent No.: 5,830,237
Issued: Nov. 3, 1998
Appl. No.: 08/611,306
Filed: Mar. 5, 1996

(51) Int. Cl.
*A61F 2/50* (2006.01)
*A61F 2/78* (2006.01)
*A61F 2/00* (2006.01)
*A61F 5/01* (2006.01)

(52) U.S. Cl. .................. 623/37; 2/22; 602/62; 623/36

(58) Field of Classification Search .................. None
See application file for complete search history.

(56) References Cited

U.S. PATENT DOCUMENTS

| | | | |
|---|---|---|---|
| 1,319,637 A | 10/1919 | Blevens |
| 1,497,219 A | 6/1924 | Martino |
| 2,002,064 A | 5/1935 | Kohl |
| 2,202,598 A | 5/1940 | Peterson |
| 2,666,208 A | 1/1954 | Funk |
| 2,703,405 A | 3/1955 | Smallberg |
| 3,084,685 A | 4/1963 | Lewis |
| 3,375,821 A | 4/1968 | Meek |
| 3,451,232 A | 6/1969 | Belzidsky |
| 3,457,566 A | 7/1969 | Artzt |
| 3,520,002 A | 7/1970 | Wellington |
| 3,600,717 A | 8/1971 | McKeehan |
| 3,663,973 A | 5/1972 | Spence |
| 3,732,578 A | 5/1973 | Pollack |
| 3,855,677 A | 12/1974 | Belzidsky |
| 3,971,194 A | 7/1976 | Morgan |
| 3,983,870 A | 10/1976 | Herbert et al. |
| 4,116,236 A | 9/1978 | Albert |
| 4,183,984 A | 1/1980 | Browers et al. |
| 4,201,203 A | 5/1980 | Applegate |
| 4,250,578 A | 2/1981 | Barlow |
| 4,369,284 A | 1/1983 | Chen |
| 4,502,234 A | 3/1985 | Schaefer et al. |

(Continued)

FOREIGN PATENT DOCUMENTS

| | | |
|---|---|---|
| DE | 4321182 C1 | 12/1994 |
| EP | 0086147 A1 | 8/1983 |
| EP | 0762857 | 11/2005 |
| EP | 1618858 | 1/2006 |
| EP | 0955964 | 10/2006 |
| EP | 1736122 | 12/2006 |
| FR | 2581859 | 11/1986 |
| GB | 2213380 A | 8/1989 |
| GB | 2261358 | 5/1993 |
| JP | 64-32861 | 2/1989 |
| SU | 1739990 A1 | 6/1992 |
| SU | 1812982 | 4/1993 |
| WO | 93/23472 | 11/1993 |
| WO | 94/24965 | 11/1994 |
| WO | 95/27756 A | 10/1995 |
| WO | 9629033 | 9/1996 |
| WO | 98/04218 | 2/1998 |

OTHER PUBLICATIONS

Silopad Silosheath Brochure (2 pp.); 2150 Liberty Drive, L.P.O. Box 211, Niagra Falls, New York, 14304; Tel.; 716–283–0700; Fax; 716–283–0600; Toll Free U.S. 1–800–229–4404; Silosheath Invoice (6 pp.) Dated Nov. 1, 1993, with photo of item No. 12155 (Silosheath/Medium; corresponding to Item No. 12155 on the Invoice); Silopos Domestic Price List (7 pp.); 2150 Liberty Drive, L.P.O. Box 211; Niagra Falls, NY 14303; Effective May 1994.

(Continued)

*Primary Examiner*—David O. Reip

(57) ABSTRACT

Articles of apparel for an amputee's residuum and for non-amputees who desire or require padding or joint support.

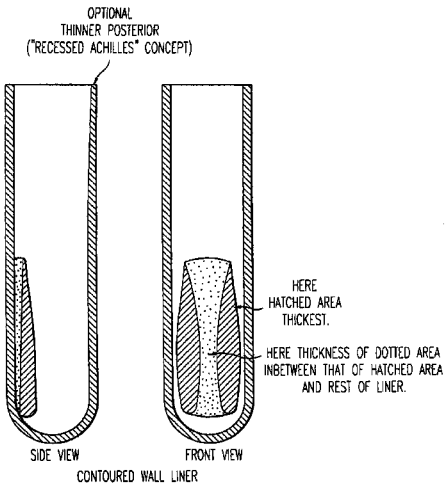

U.S. PATENT DOCUMENTS

| Patent | Date | Inventor |
|---|---|---|
| 4,517,688 A | 5/1985 | May et al. |
| 4,590,123 A | 5/1986 | Hashimoto et al. |
| 4,618,213 A | 10/1986 | Chen |
| 4,635,626 A | 1/1987 | Lerman |
| 4,671,267 A | 6/1987 | Stout |
| 4,814,375 A | 3/1989 | Esposito |
| 4,822,371 A | 4/1989 | Jolly |
| 4,832,010 A | 5/1989 | Lerman |
| 4,840,635 A | 6/1989 | Smith et al. |
| 4,842,931 A | 6/1989 | Zook |
| 4,908,037 A | 3/1990 | Ross |
| 4,923,474 A | 5/1990 | Klasson et al. |
| 4,923,475 A | 5/1990 | Gosthanian et al. |
| 5,007,937 A | 4/1991 | Fishman et al. |
| 5,098,421 A | 3/1992 | Zook |
| 5,108,456 A | 4/1992 | Coonan |
| 5,154,690 A | 10/1992 | Shiono |
| 5,201,773 A | 4/1993 | Carideo |
| 5,201,774 A | 4/1993 | Greene |
| 5,211,667 A | 5/1993 | Danforth |
| 5,218,056 A | 6/1993 | Santiyanont et al. |
| 5,221,534 A | 6/1993 | DesLauriers et al. |
| 5,246,464 A | 9/1993 | Sabolich |
| 5,258,036 A | 11/1993 | Edenbaum et al. |
| 5,258,037 A | 11/1993 | Caspers |
| 5,262,468 A | 11/1993 | Chen |
| 5,263,923 A | 11/1993 | Fujimoto |
| 5,263,990 A | 11/1993 | Handal |
| 5,314,496 A | 5/1994 | Harris et al. |
| 5,314,497 A | 5/1994 | Fay et al. |
| 5,334,646 A | 8/1994 | Chen |
| 5,336,708 A | 8/1994 | Chen |
| 5,376,131 A | 12/1994 | Lenze et al. |
| 5,376,132 A | 12/1994 | Caspers |
| 5,387,245 A | 2/1995 | Fay et al. |
| 5,405,405 A | 4/1995 | Love |
| 5,411,037 A | 5/1995 | Hess et al. |
| 5,443,525 A | 8/1995 | Laghi |
| 5,464,384 A | 11/1995 | Cromartie |
| 5,464,443 A | 11/1995 | Wilson et al. |
| 5,480,455 A | 1/1996 | Norvell |
| 5,497,789 A | 3/1996 | Zook |
| 5,507,834 A | 4/1996 | Laghi |
| 5,508,334 A | 4/1996 | Chen |
| 5,534,496 A | 7/1996 | Lee et al. |
| 5,538,500 A | 7/1996 | Peterson |
| 5,555,584 A | 9/1996 | Moore et al. |
| 5,571,208 A | 11/1996 | Caspers |
| 5,593,454 A | 1/1997 | Helmy |
| 5,603,122 A | 2/1997 | Kania |
| 5,633,286 A | 5/1997 | Chen |
| 5,656,023 A | 8/1997 | Caprio et al. |
| 5,728,167 A | 3/1998 | Lohmann |
| 5,769,809 A | 6/1998 | Witzel |
| 5,792,531 A | 8/1998 | Littleton et al. |
| 5,830,237 A | 11/1998 | Kania |
| 5,854,372 A | 12/1998 | Henze et al. |
| 6,025,067 A | 2/2000 | Fay |
| 6,063,125 A | 5/2000 | Arbogast et al. |
| 6,117,176 A | 9/2000 | Chen |
| 6,136,039 A | 10/2000 | Kristinsson et al. |
| 6,231,617 B1 | 5/2001 | Fay |
| 6,406,499 B1 | 6/2002 | Kania |
| 6,440,345 B1 | 8/2002 | Hellberg |
| 6,592,539 B1 | 7/2003 | Einarsson et al. |
| 6,761,742 B2 | 7/2004 | Caspers |
| 6,964,688 B1 | 11/2005 | Kania |
| 2002/0183859 A1 | 12/2002 | Houser |
| 2005/0020951 A1 | 1/2005 | Gaylord et al. |

OTHER PUBLICATIONS

Silosheath Classic Apr. 30, 2001 Webpage Printout (2 pp.).

Silosheath Soft Socket Gel Liner Brochure (2 pp.) Prices good from Mar. 15, 1994 to Jun. 15, 1994; Silipos, 2150 Liberty Drive, L.P.O. Box 211; Niagara Falls, NY 14304; Toll free: 1–800–229–4404.

SiloLiner Brochure (4 pp.); Silipos, 7049 Williams Road; L.P.O. Box 211; Niagara Falls, NY 14304; Toll free: 1–800–229–4404.

SiloLiner, Mar. 8, 1999 Webpage Printout (2 pp.).

SiloLiner, Feb. 1999 Brochure (2 pp.); Silipos, 7049 Williams Road; L.P.O Box 211; Niagara Falls, NY 14304; Toll free: 1–800–229–4404; www.silipos.com.

Silopos Special! Advertisement, Offer Good through Nov. 30, 1994, (1 pp.) Knit–Rite, Incorporated, 2020 Grand Avenue, P.O. Box 410208, Kansas City, MO 64141–0208: (816) 221–5200; Fax: (816) 221–2896.

Pel Supply Co., Prosthetic Catalog, 1994, 75 pages (previously submitted by Requester in Reexamination 90/008, 257).

Iceflex Endurance Brochure (2 pp.); Distributors in the United States and Canada (1) Cascade, Tel: 800–888–0865; (2) Knit–Rite, Tel: 800–821–3094; (3) Orto–Ped, Tel: 800–363–8726; (4) PEL, Tel: 800–321–1264; (5) SPS, Tel: 800–767–7776.

IPOS Orthopaie Industriell Brochure, The advantages of the ipocon compression sheath, (2 pp.).

Alpha Cushion and Locking Liner Brochures (Jan. 14, 1997); (8 pp.) Ohio Willow Wood Company; 15441 Scioto Darby Road; P.O. Box 130; Mt. Sterling, OH 43143; Tel: 800–848–4930.

Luxury Liner Brochure The Maximum Comfort Sleeve (4 pp.); 180 N. San Gabriel Blvd., Pasadena, CA 91107–3488 USA, P.O. Box 5030, Pasadena, CA 91117–0030; www.usms.com; Tel: (818) 796–0477; Fax: (818) 440–9533.

Alps ClearSheath Silicone Sheaths (1 pp.); Alps South Corp.; 6504 44th Street N., Pinellas Park FL 34664; Tel: 1–800–574–5426; (813) 528–8566; Fax: (816) 528–8862.

Alps BetaLiner. . . with Gel and Spandex for Extraordinary Comfort & Cushioning (1 pp.); Alps South Corp.; 2895 42nd Ave. N., St. Petersburg, FL 33714; Tel: (813) 528–8566; 1–800–574–5426; Fax: (813) 528–8862; www.oandp.com/alps.

Alps Gel–Sheath (1 pp.); Faxed Jul. 24, 2997; Alps South Corp.; 2895 42nd Ave. N., St. Petersburg, FL 33714; Tel: (813) 528–8566; 1–800–574–5426; Fax: (813) 528–8862; www.oandp.com/alps.

Introducing Alps GelSock . . . with a Gel Interlayer for Extraordinary Comfort & Cushioning (1 pp.); Alps South Corp.; 2895 42nd Ave. N., St. Petersburg, FL 33714; Tel: (813) 528–8566; 1–800–574–5426; Fax: (813) 528–8862; www.oandp.com/alps.

New! The TEC Profile (2 pp.); 820 Sundial Drive, Waite Park, MN 56387; Tel: 320–259–4853; 1–800–688–4832; Fax: (320) 251–0110; www.tecinterface.com.

TEC Interface Systems Accident (12 pp.).

Total Environmental Control . . . Again and Again!, (4 pages), 510 North 25th Avenue, St. Cloud, MN 56303–4832.

New Products from Ossur, Iceross, Comfort TM, "The Ultimate in Silicone Gel Suspension From Ossur, the Silicone Specialist," (1 pp.), Nov. 1997, Distributed by : SPS Orthotic Prosthetic Supplies (800–767–7776).

Otto Bock Gel–Strumpf, Derma Seal, Advertisement, Unknown Place of Publication, Unknown date.

O&P Business News dated Sep. 1, 1994 (Advertisement of Silipos, p. 9).
O&P Business News dated Oct. 1, 1994 (Advertisement of Silipos).
O&P Business News dated Jan. 1, 1995 (Advertisement of Silipos, p. 16).

1994 Catalog of Silipos Advanced Polymer Technology.
Handbook of Thermoplastic Elastomers (pp. 72–102) (Van Nostrand Reinhold Company, 1979) New York, NY, U.S.A.
Shell Company Technical Bulletin SC: 1102–89 "Kraton (R) Thermoplastic Rubber in Oil Gels," dated Apr. 1989 (U.S.A.).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 3 are determined to be patentable as amended.

Claims 2, 4, 6–8, 12–16 and 18–23, dependent on an amended claim, are determined to be patentable.

Claims 5, 9–11 and 17 were not reexamined.

1. A tube sock-shaped covering for enclosing an amputation stump, said covering having an open end for introduction of said stump and a closed end opposite said open end, said covering comprising fabric in the shape of a tube sock [coated on only one side] *and having a coating of polymeric material residing on only an interior surface* thereof [with], *said polymeric material comprising* a foamed or non-foamed gel composition comprising a block copolymer and mineral oil.

3. The tube sock-shaped covering of claim 1, wherein said gel coating is [on the inside of said covering and is] arranged in a recessed achilles configuration.

* * * * *

EX PARTE REEXAMINATION CERTIFICATE (8723rd)

United States Patent
Kania

(10) Number: US 5,830,237 C2
(45) Certificate Issued: Nov. 29, 2011

(54) GEL AND CUSHIONING DEVICES

(75) Inventor: Bruce G. Kania, Bozeman, MT (US)

(73) Assignee: The Ohio Willow Wood Company, Mt. Sterling, OH (US)

Reexamination Request:
No. 90/009,268, Sep. 8, 2008

Reexamination Certificate for:
Patent No.: 5,830,237
Issued: Nov. 3, 1998
Appl. No.: 08/611,306
Filed: Mar. 5, 1996

Reexamination Certificate C1 5,830,237 issued Sep. 2, 2008

(51) Int. Cl.
*A61F 2/78* (2006.01)

(52) U.S. Cl. .............. 623/37; 623/36; 602/62; 2/22

(58) Field of Classification Search .............. None
See application file for complete search history.

(56) References Cited

To view the complete listing of prior art documents cited during the proceedings for Reexamination Control Numbers 90/009,268 and 90/008,277, please refer to the USPTO's public Patent Application Information Retrieval (PAIR) system under the Display References tab.

*Primary Examiner* — Jeffrey R. Jastrzab

(57) ABSTRACT

Articles of apparel for an amputee's residuum and for non-amputees who desire or require padding or joint support.

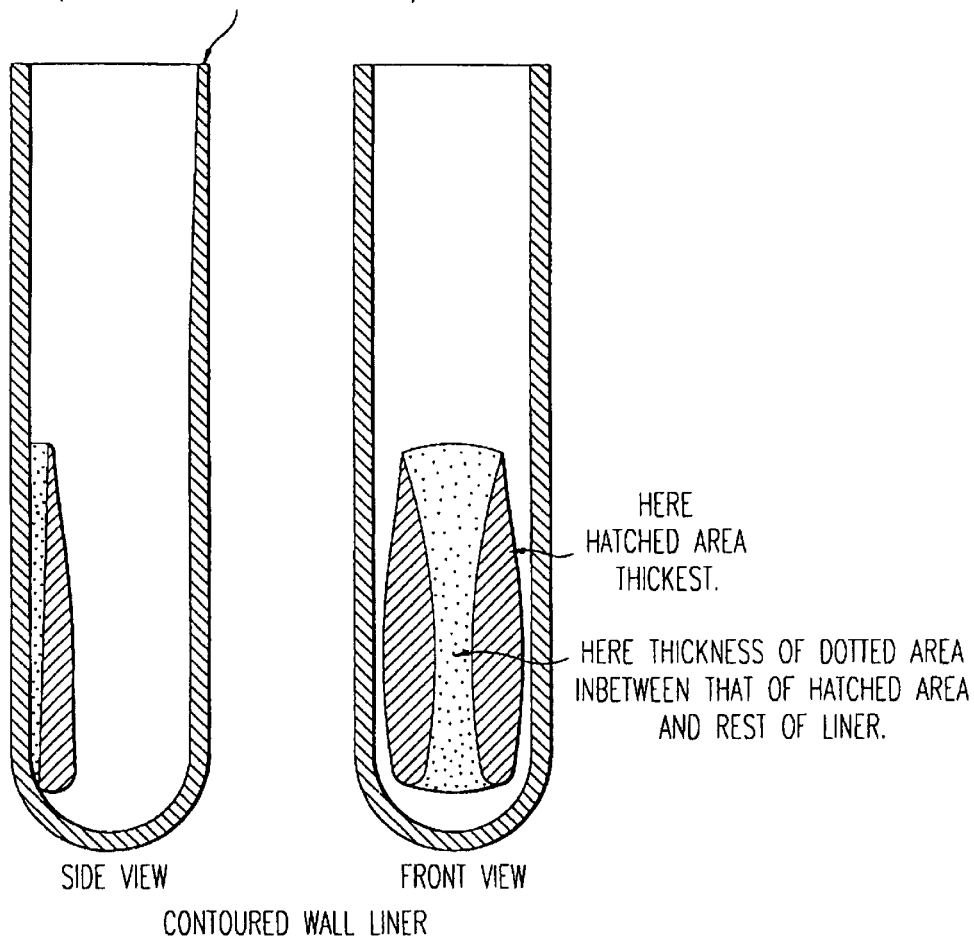

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-23, dependent on an amended claim, are determined to be patentable.

1. A tube sock-shaped covering for enclosing an amputation stump, *said amputation stump being a residual limb*, said covering having an open end for introduction of said [stump] *residual limb* and a closed end opposite said open end, said covering comprising fabric in the shape of a tube sock[and], *said fabric* having a coating of [polymeric material] *a foamed or non-foamed block copolymer and mineral oil gel composition* residing on only an interior surface thereof[, said polymeric material comprising a foamed or non-foamed gel composition comprising a block copolymer and mineral oil].

* * * * *